United States Patent [19]

Wehner

[11] Patent Number: 4,786,672

[45] Date of Patent: Nov. 22, 1988

[54] ANILINOTRIAZINES AND THE USE THEREOF

[75] Inventor: Wolfgang Wehner, Zwingenberg, Fed. Rep. of Germany

[73] Assignee: Ciba-Geigy Corporation, Ardsley, N.Y.

[21] Appl. No.: 76,246

[22] Filed: Jul. 21, 1987

[30] Foreign Application Priority Data

Jul. 31, 1986 [CH] Switzerland ............. 3083/86

[51] Int. Cl.$^4$ ............. C08K 5/34; C08K 5/09; C08K 5/11; C08L 61/28
[52] U.S. Cl. ............. 524/100; 524/396; 524/399; 524/400; 524/147; 524/151; 524/109
[58] Field of Search ............. 524/100, 396, 399, 400; 544/197

[56] References Cited

U.S. PATENT DOCUMENTS

| | | | |
|---|---|---|---|
| 2,861,070 | 11/1958 | Rademacher | 544/197 |
| 3,290,307 | 12/1966 | Keller et al. | 544/197 |
| 3,312,698 | 4/1967 | Dazzi et al. | 544/197 |
| 3,496,136 | 2/1970 | Susi et al. | 524/100 |
| 3,714,119 | 1/1973 | Stretanski | 524/100 |
| 4,183,875 | 1/1980 | Eckelt et al. | 524/100 |
| 4,297,492 | 10/1981 | Rasberger et al. | 544/197 |

FOREIGN PATENT DOCUMENTS 3512446 10/1986 Fed. Rep. of Germany ...... 544/197

OTHER PUBLICATIONS

D. F. Walker et al., J. Am. Pharm. Assn., 39, 393 (1950).
D. W. Kaiser et al., J. Am. Chem. Soc., 73, 2984 (1951).
Chem. Abstract 99, 176847q (1983).

Primary Examiner—Kriellion Morgan

Attorney, Agent, or Firm—Luther A. R. Hall

[57] ABSTRACT

Stabilized chlorine-containing polymers containing at least one anilinotriazine of the formula I

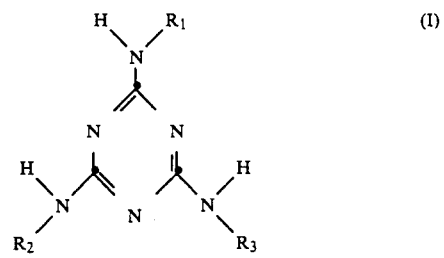

in which $R_1$ is phenyl or a group of the formula II

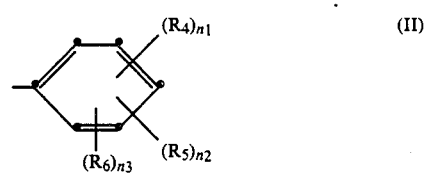

in which $R_4$, $R_5$ and $R_6$ independently of one another are chlorine, bromine, cyano, methoxycarbonyl, ethoxycarbonyl, carbamoyl, hydroxyl, methoxy, ethoxy or $C_1$-$C_{18}$-alkyl and $n_1$, $n_2$ and $n_3$ are 0, 1, 2, or 3, subject to the proviso that the sum of $n_1+n_2+n_3$ is an integer from 1 to 3, and $R_2$ and $R_3$ independently of one another are $C_2$-$C_4$-hydroxyalkyl, and also novel anilinotriazines and the use thereof for stabilizing chlorine-containing polymers against the harmful effects of light and/or heat.

12 Claims, No Drawings

ANILINOTRIAZINES AND THE USE THEREOF

The present invention relates to chlorine-containing polymers which have been stabilized with anilinotriazines and to novel anilinotriazines and the use thereof for stabilizing chlorine-containing polymers against the harmful effects of light and/or heat.

The use of substituted melamines for stabilizing pigmented polyvinyl chloride is described in U.S. Pat. No. 3,714,114. A stabilizer composition containing (a) a substituted melamine and (b) a substance which absorbs UV light is also disclosed in U.S. Pat. No. 3,496,136.

The preparation of 2-anilino-4,6-bis-(2-hydroxyethylamino)-1,3,5-triazine and of similar compounds was described as early as 1950 by D. F. Walker et al. in the "Journal of the American Pharmaceutical Association, Volume 39, pages 393–396" and in 1951 by D. W. Kaiser et al. in the "Journal of the American Chemical Society, Volume 73, pages 2984–2986.

The invention relates to a chlorine-containing polymer containing at least one compound of the formula I

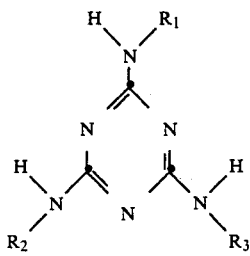

in which $R_1$ is phenyl or a group of the formula II

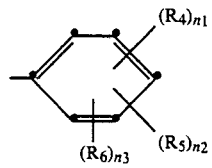

in which $R_4$, $R_5$ and $R_6$ independently of one another are chlorine, bromine, cyano, methoxycarbonyl, ethoxycarbonyl, carbamoyl, hydroxyl, methoxy, ethoxy or $C_1$–$C_8$-alkyl and $n_1$, $n_2$ and $n_3$ are 0, 1, 2 or 3, subject to the proviso that the sum of $n_1+n_2+n_3$ is an integer from 1 to 3, and $R_2$ and $R_3$ independently of one another are $C_2$–$C_4$-hydroxyalkyl.

The anilinotriazines of the formula I have a particularly advantageous effect on the colour stability of chlorine-containing polymers when the latter are processed by thermoplastic methods and are exposed to light.

Examples of $R_1$ as a group of the formula II are o-, m- or p-chlorophenyl, 2,3-dichlorophenyl, 2,4-dichlorophenyl, 2,5-dichlorophenyl, 2,6-dichlorophenyl, 3,4-dichlorophenyl, 2,4,5-trichlorophenyl, 2,4,6-trichlorophenyl, o-, m- or p-hydroxyphenyl, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 2-methyl-4-tert.-butylphenyl, 2-ethylphenyl, 2,6-diethylphenyl, 2,6-diethyl-4-methylphenyl, 2,6-diisopropylphenyl, 4-tert.-butylphenyl, o-, m- or p-(n-dodecyl)phenyl, 2-chloro-6-methyl, 3-chloro-2-methylphenyl, 3-chloro-4-methylphenyl, 4-chloro-2-methylphenyl, 5-chloro-2-methylphenyl, 2,6-dichloro-3-methylphenyl, 2-hydroxy-4-methylphenyl, 3-hydroxy-4-methylphenyl, o-, m- or p-methoxyphenyl, o- or p-ethoxyphenyl, 2,4-dimethoxyphenyl, 2,5-dimethoxyphenyl, 2,5-diethoxyphenyl, 2-methoxy-5-methylphenyl, 4-methoxy-2-methylphenyl, 3-chloro-4-methoxyphenyl, 3-chloro-6-methoxyphenyl, 3-chloro-4,6-dimethoxyphenyl or 4-chloro-2,5-dimethoxyphenyl. Phenyl radicals containing at least one methoxy group are preferred. o-, m- or p-chlorophenyl and o-, m- or p-hydroxyphenyl are particularly preferred.

Examples of $R_2$ and $R_3$ as $C_2$–$C_4$-hydroxyalkyl are 2-hydroxyethyl, 2-hydroxypropyl, 3-hydroxypropyl, 1-hydroxymethylethyl, 3-hydroxybutyl, 1,1-dimethyl-2-hydroxyethyl or 4-hydroxybutyl. 2-Hydroxyethyl is preferred.

The invention preferably relates to a chlorine-containing polymer containing at least one compound of the formula I in which $R_1$ is phenyl or a group of the formula II in which $R_4$, $R_5$ and $R_6$ independently of one another are chlorine, bromine, hydroxyl, methoxy, ethoxy or $C_1$–$C_8$-alkyl.

A chlorine-containing polymer which is of interest contains at least one compound of the formula I in which $R_1$ is phenyl or a group of the formula II in which $R_4$, $R_5$ and $R_6$ independently of one another are chlorine, hydroxyl, methoxy, ethoxy or $C_1$–$C_{12}$-alkyl.

A preferred chlorine-containing polymer contains at least one compound of the formula I in which $R_1$ is phenyl or a group of the formula II in which $R_4$, $R_5$ and $R_6$ independently of one another are chlorine, hydroxyl, methoxy or methyl.

The invention also preferably relates to a chlorine-containing polymer containing at least one compound of the formula I in which $R_1$ is phenyl or a group of the formula II in which $R_4$, $R_5$ and $R_6$ independently of one another are chlorine or hydroxyl.

An equally preferred chlorine-containing polymer contains at least one compound of the formula I in which $R_1$ is phenyl or a group of the formula II in which the radicals $R_4$, $R_5$ and $R_6$ are identical.

A chlorine-containing polymer which is of particular interest contains at least one compound of the formula I in which $R_1$ is phenyl or a group of the formula II in which $n_1$ and $n_2$ are 0 and $n_3$ is 1.

A particularly preferred chlorine-containing polymer contains at least one compound of the formula I in which $R_1$ is phenyl.

A chlorine-containing polymer which is also of interest contains at least one compound of the formula I in which $R_2$ and $R_3$ are 2-hydroxyethyl.

The chlorine-containing polymers are preferably vinyl chloride homopolymers or copolymers. Suspension and mass polymers, as well as emulsion polymers, are also preferred. The following are examples of comonomers suitable for the copolymers: vinyl acetate, vinylidene chloride, trans-dichloroethene, ethylene, propylene, butylene, maleic acid, acrylic acid, fumaric acid and itaconic acid. Other suitable chlorine-containing polymers are post-chlorinated PVC and chlorinated polyolefines and also graft polymers of PVC containing EVA, ABS and MBS.

The compounds of the formula I are particularly suitable for stabilizing polyvinyl chloride.

It is advantageous if the chlorine-containing polymers according to the invention contain, in addition, at least one conventional heat stabilizer. Examples of such stabilizers are mentioned in "Pure & Appl. Chem., 49, 627–648 (1977)". Examples of heat stabilizers are Me(II) carboxylates and Me(II) phenates, in which Me(II) can be Mg, Ca, Ba, Zn or Cd and carboxylate can be, for example, stearate, oleate, laurate, palmitate, behenate, benzoate, hydroxystearate or 2-ethylhexanoate, and also alkylphenates, in particular nonylphenate, and organotin compounds. The following may be mentioned as examples of organotin compounds: n-octyl tin tris-[isooctylthioglycollate], di-n-octyl tin bis-[isooctylthioglycollate], dibutyltin sulfide, dibutyltin thioglycollate or butyltin sulfide and also methyl tin tris-[alkylthioglycollate], n-butyltin tris-[alkylthioglycollate], n-butoxycarbonylethyltin tris-[alkylthioglycollate], dimethyl tin bis-[alkylthioglycollate], di-n-butyltin bis-[alkylthioglycollate], bis-[n-butoxycarbonylethyl]-tin bis-[alkylthioglycollate], methyltin tris-[alkylthiopropionate], n-butyltin tris-[alkylthiopropionate], n-butoxycarbonylethyltin tris-[alkylthiopropionate], dimethyltin bis-[alkylthiopropionate], di-n-butyltin bis-[alkylthiopropionate] and bis-[n-butoxycarbonylethyl]-tin bis-[alkylthiopropionate] in which alkyl is, for example, 2-ethylhexyl, dodecyl, tridecyl or tetradecyl, and also organotin carboxylates, in particular maleates or halfester maleates.

The invention therefore also relates to a chlorine-containing polymer containing at least one compound of the formula I and, in addition, at least one Me(II) carboxylate and/or Me(II) phenate or alkylphenate in which Me(II) is Mg, Ca, Ba, Zn or Cd and carboxylate is the anion of a carboxylic acid having 7 to 20C atoms.

Examples of $C_7$–$C_{20}$-carboxylic acids are benzoic acid, p-tert.-butylbenzoic acid or aliphatic carboxylic acids, in particular octanoic acid, dodecanoic acid, stearic acid or oleic acid.

Chlorine-containing polymers containing a compound of the formula I and, in addition, a mixture of barium/zinc, calcium/zinc or magnesium/zinc carboxylates are of particular interest.

The invention also relates to the use of a compound of the formula I for stabilizing a chlorine-containing polymer against the harmful effects of light and/or heat.

The incorporation of the stabilizer components into the chlorine-containing polymer is most advantageously effected in the customary manner on a twin-roll mill at temperatures between 150° and 200° C. In general, adequate homogenization can be achieved within 5 to 15 minutes. The components can be added individually or together in the form of a premix. A liquid premix has proved advantageous, i.e. incorporation is carried out in the presence of inert solvents and/or plasticizers.

The Me(II) carboxylates, Me(II) phenates or Me(II) alkylphenates can be present in the material to be stabilized in a concentration known to those skilled in the art, for example in amounts of 0.05 to 5% by weight.

For example, the compound of the formula I is incorporated into the chlorine-containing polymer in amounts of 0.05 to 10, preferably 0.1 to 5 and particularly preferably 0.1 to 2, % by weight.

The term % by weight relates in each case to the material to be stabilized.

In addition, the chlorine-containing polymers can contain customary amounts of conventional PVC stabilizers, for example epoxy compounds, preferably epoxidized fatty acid esters, such as epoxidized soya bean oil, phenolic antioxidants or phosphites, for example trioctyl, tridecyl, tridodecyl, tritetradecyl, tristearyl, trioleyl, triphenyl, tricresyl, tris-[p-nonylphenyl] or tricyclohexyl phosphite and, particularly preferably, aryl dialkyl phosphites and alkyl diaryl phosphites, for example phenyl didecyl phosphite, nonylphenyl didecyl phosphite, (2,4-di-tert.-butylphenyl)didodecyl phosphite or (2,6-di-tert.-butylphenyl)didodecyl phosphite.

Depending on the end use of the polymers, it is also possible to incorporate, before or during the incorporation of the stabilizers, further additives, for example lubricants (preferably montan waxes or glycerol esters), fatty acid esters, paraffins, plasticizers (for example esters of phthalic acid, phosphoric acid, adipic acid, azelaic acid, sebacic acid and citric acid), fillers, carbon black, asbestos, kaolin, talc, glass fibres, modifiers (for instance high impact strength additives), fluorescent brighteners, pigments, light stabilizers, UV absorbers, fire-retarding agents of antistatic agents.

The invention also relates to the novel compounds of the formula IA

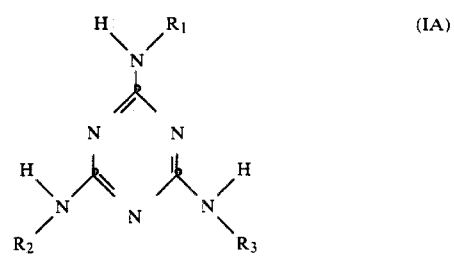

in which $R_1$ is a group of the formula II

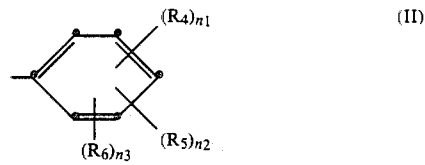

in which $R_4$, $R_5$ and $R_6$ independently of one another are chlorine, bromine, cyano, methoxycarbonyl, ethoxycarbonyl, carbamoyl, hydroxyl, methoxy, ethoxy or $C_1$–$C_{18}$-alkyl and $n_1$, $n_2$ and $n_3$ are 0, 1, 2 or 3, subject to the proviso that the sum of $n_1+n_2+n_3$ is an integer from 1 to 3, and $R_2$ and $R_3$ independently of one another are $C_2$–$C_4$-hydroxyalkyl.

This invention also preferably relates to compounds of the formula IA in which $R_4$, $R_5$ and $R_6$ independently of one another are chlorine, bromine, hydroxyl, methoxy, ethoxy or $C_1$–$C_{18}$-alkyl.

Preferred compounds of the formula IA are those in which $R_4$, $R_5$ and $R_6$ independently of one another are chlorine, hydroxyl, methoxy, ethoxy or $C_1$–$C_{12}$-alkyl, especially chlorine or hydroxyl.

Compounds of the formula IA which are also preferred are those in which $R_4$, $R_5$ and $R_6$ independently of one another are chlorine, hydroxyl, methoxy or methyl. It is particularly preferable for the radicals $R_4$, $R_5$ and $R_6$ to be identical.

Compounds of the formula IA in which $n_1$ and $n_2$ are 0 and $n_3$ is 1 are of interest.

Compounds of the formula IA in which $R_2$ and $R_3$ are 2-hydroxyethyl are of particular interest.

The following are examples of compounds of the formula IA:

2,4-bis-(2-hydroxyethylamino)-6-(2-chloroanilino)-1,3,5-triazine, 2,4-bis-(2-hydroxyethylamino)-6-(3-chloroanilino)-1,3,5-triazine,
2,4-bis-(2-hydroxyethylamino)-6-(4-chloroanilino)-1,3,5-triazine,
2,4-bis-(2-hydroxyethylamino)-6-(2-methoxyanilino)-1,3,5-triazine,
2,4-bis-(2-hydroxyethylamino)-6-(3-methoxynilino)-1,3,5-triazine,
2,4-bis-(2-hydroxyethylamino)-6-(4-methoxyanilino)-1,3,5-triazine,
2,4-bis-(2-hydroxyethylamino)-6-(2-ethoxyanilino)-1,3,5-triazine,
2,4-bis-(2-hydroxyethylamino)-6-(3-ethoxyanilino)-1,3,5-triazine,
2,4-bis-(2-hydroxyethylamino)-6-(2,4-dimethoxyanilino)-1,3,5-triazine,
2,4-bis-(2-hydroxyethylamino)-6-(2,5-dimethoxyanilino)-1,3,5-triazine,
2,4-bis-(2-hydroxyethylamino)-6-(3,4-dimethoxyanilino)-1,3,5-triazine,
2,4-bis-(2-hydroxyethylamino)-6-(3,5-dimethoxyanilino)-1,3,5-triazine,
2,4-bis-(2-hydroxyethylamino)-6-(4-ethoxyanilino)-1,3,5-triazine,
2,4-bis-(2-hydroxyethylamino)-6-(2-n-dodecylanilino)-1,3,5-triazine,
2,4-bis-(2-hydroxyethylamino)-6-(3-n-dodecylanilino)-1,3,5-triazine,
2,4-bis-(2-hydroxyethylamino)-6-(4-n-dodecylanilino)-1,3,5-triazine,
2,4-bis-(2-hydroxyethylamino)-6-(2-hydroxyanilino)-1,3,5-triazine,
2,4-bis-(2-hydroxyethylamino)-6-(3-hydroxyanilino)-1,3,5-triazine,
2,4-bis-(2-hydroxyethylamino)-6-(4-hydroxyanilino)-1,3,5-triazine,
2,4-bis-(2-hydroxyethylamino)-6-(3-hydroxy-4-methoxyanilino)-1,3,5-triazine,
2,4-bis-(2-hydroxyethylamino)-6-(2-methylanilino)-1,3,5-triazine,
2,4-bis-(2-hydroxyethylamino)-6-(3-methylanilino)-1,3,5-triazine,
2,4-bis-(2-hydroxyethylamino)-6-(4-methylanilino)-1,3,5-triazine,
2,4-bis-(2-hydroxyethylamino)-6-(2-ethylanilino)-1,3,5-triazine,
2,4-bis-(2-hydroxyethylamino)-6-(3-ethylanilino)-1,3,5-triazine,
2,4-bis-(2-hydroxyethylamino)-6-(4-ethylanilino)-1,3,5-triazine,
2,4-bis-(2-hydroxyethylamino)-6-(2-propylanilino)-1,3,5-triazine,
2,4-bis-(2-hydroxyethylamino)-6-(4-propylanilino)-1,3,5-triazine,
2,4-bis-(2-hydroxyethylamino)-6-(4-n-butylanilino)-1,3,5-triazine,
2,4-bis-(2-hydroxyethylamino)-6-(4-tert.-butylanilino)-1,3,5-triazine and
2,4-bis-(2-hydroxyethylamino)-6-(4-octylanilino)-1,3,5-triazine.

2,4-bis-(2-Hydroxyethylamino)-6-(3-hydroxyanilino)-1,3,5-triazine, 2,4-bis-(2-hydroxyethylamino)-6-(2-chloroanilino)-1,3,5-triazine, 2,4-bis-(2-hydroxyethylamino)-6-(3-chloroanilino)-1,3,5-triazine, 2,4-bis-(2-hydroxyethylamino)-6-(4-chloroanilino)-1,3,5-triazine and 2,4-bis-(2-hydroxyethylamino)-6-(3-methoxyanilino)-1,3,5-triazine are particularly preferred.

The compounds of the formulae I and IA can be prepared in a manner know per se, for example as described in an article by D. W. Kaiser et al. in the "Journal of the American Chemical Society, 73, 2984 (1951)", by reacting a compound of the formula III

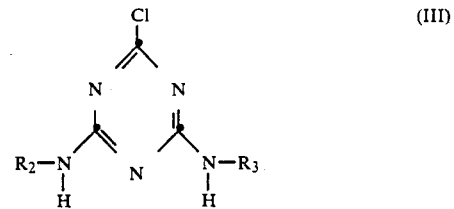

in which $R_2$ and $R_3$ are as defined above, in an aqueous solution in the presence of NaOH, with aniline or an aniline derivative of the formula IV

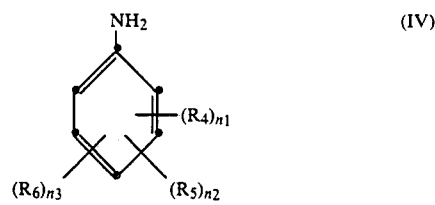

in which $R_4$, $R_5$, $R_6$, $n_1$, $n_2$ and $n_3$ are as defined in the preceding statements. It is advantageous to carry out the reaction at a temperature between 80° and 100° C.

The compounds of the formula III can be prepared analogously to known processes, for example by reacting cyanuric chloride (dissolved in acetone) with $H_2NR_2$ or $H_2NR_3$ in the presence of sodium hydroxide. It is advantageous to use an aqueous solution as the reaction medium. The temperature is preferably between 0° and 30° C.

The aniline derivatives of the formula IV are known (and are for the most part commercially available) and can also be prepared analogously to known processes.

The following examples illustrate the invention further. In these, and also in the remainder of the description, parts and percentages are by weight, unless stated otherwise.

EXAMPLE 1

Preparation of 2,4-bis-(2-hydroxyethylamino)-6-anilino-1,3,5-triazine 33 g of ice and 67 ml of water are placed in a 500 ml flask equipped with a stirrer, a reflux condenser and a thermometer. A solution of 31.0 g (0.168 mol) of cyanuric chloride in 75 ml of acetone is added dropwise with vigorous stirring, to obtain a fine suspension. 20.5 g (0.336 mol) of ethanolamine are added dropwise to this suspension, also with stirring, and the solution, which is now virtually clear, is allowed to reach room temperature. A solution of 13.4 g of sodium hydroxide in 50 ml of water is then added dropwise at such a rate that the pH does not exceed a value of 7. When the addition is complete, the pH is 6.85. The resulting precipitate is filtered off and washed until free from chloride. The product (2,4-bis-(2-hydroxyethylamino)-6-chloro-1,3,5-triazine) is suspended, while still moist, in 200 ml of water. 14.7 g (0.158 mol) of aniline are added dropwise, with stirring, and the mixture is heated to 90° C. This gives a clear solution. 6.0 g of sodium hydroxide, dissolved in 50 ml of water, are then added and the reaction solution is heated under reflux for 3 hours. 75 ml of isopropanol are then added to the slightly cloudy solution while it is still hot. The solution, which is now clear, is cooled slowly to 0° C., which precipitates a thick mash of crystals. The precipitate is filtered off with suction, washed free from chloride with a little cold water and dried. The product has a melting point of 120°–122° C. The yield is 39.2 g (=90.1% of theory).

If the product is recrystallized from 200 ml of isopropanol, the melting point rises to 128°–130° C.

EXAMPLE 2

Preparation of 2,4-bis-(2-hydroxyethylamino)-6-(3-hydroxyanilino)-1,3,5-triazine 70.1 g (0.3 mol) of 2,4-bis-(2-hydroxyethylamino)-6-chloro-1,3,5-triazine, 32.8 g (0.3 mol) of 3-hydroxyaniline and 400 ml of water are placed in a 2 l flask equipped with a stirrer, a dropping funnel, a reflux condenser and a thermometer. The mixture is heated under reflux, with stirring. In the course of this, a solution of 12 g of sodium hydroxide in 60 ml of water is added dropwise slowly at such a rate that a slightly alkaline reaction mixture results. 300 ml of water are then added, as well as active charcoal for the removal of colour. The hot solution is then filtered and cooled. The resulting, virtually colourless crystals are filtered off with suction, washed free from chloride with a little water and dried. The product has a melting point of 142°–143° C. The yield is 70.8 g (=77% of theory).

EXAMPLE 3

Preparation of 2,4-bis-(2-hydroxyethylamino)-6-(2-chloroanilino)-1,3,5-triazine 6.8 g (0.053 mol) of 2,4-bis-(2-hydroxyethylamino)-6-chloro-1,3,5-triazine, 11.7 g (0.05 mol) of 2-chloroaniline and 85 ml of water are placed in a 250 ml flask equipped with a stirrer, a dropping funnel, a reflux condenser and a thermometer. The mixture is heated with stirring to 90° C., in the course of which a clear solution is formed. A solution of 2 g of sodium hydroxide in 15 ml of water is added dropwise to this mixture, and the whole mixture is heated under reflux for 3 hours. After cooling, the aqueous system is in 2 phases. The supernatant inorganic phase is discarded. The lower phase is extracted by boiling with toluene, the product being obtained in the residue. The melting point is 108°–110° C. and, after reprecipitation with ethyl acetate/petroleum ether, is 112°–114° C. The yield is 82% of theory.

EXAMPLE 4

Preparation of 2,4-bis-(2-hydroxyethylamino)-6-(3-chloroanilino)-1,3,5-triazine

The preparation is carried out analogously to Example 3, employing 3-chloroaniline instead of 2-chloroaniline. The product has a melting point of 134°–136° C. The yield is 79% of theory.

EXAMPLE 5

Preparation of 2,4-bis-(2-hydroxyethylamino)-6-(4-chloroanilino)-1,3,5-triazine

The preparation is carried out analogously to Example 3, employing 4-chloroaniline instead of 2-chloroaniline and, when the reaction is complete, treating the lower phase with isopropanol (recrystallization) instead of toluene. The product has a melting point of 150°–152° C. The yield is 72% of theory.

EXAMPLES 6–12:

The compounds of the formula

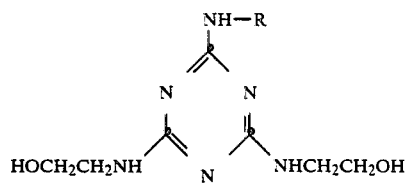

are prepared analogously to Example 3. When the addition of NaOH is complete and the mixture has been heated under reflux, the resulting solid is separated off, washed with water and dried to constant weight.

| Example | R | Yield [% of theory] | Melting point [°C.] | Colour |
|---|---|---|---|---|
| 6 | ⟨phenyl with H₃C⟩ | 69 | 80 | beige |
| 7 | ⟨phenyl with CH₃⟩ | 90 | 80 | beige |
| 8 | ⟨phenyl–CH₃⟩ | 81 | 140 | colourless |
| 9 | ⟨phenyl with OCH₃⟩ | 84 | 130 | colourless |
| 10 | ⟨phenyl–OCH₃⟩ | 74* | 185 | colourless |
| 11 | ⟨phenyl–OCH₃ with OH⟩ | 60** | 160 | beige |
| 12 | ⟨phenyl–OCH₃ with OCH₃⟩ | 44*** | 125 | colourless |

*after reprecipitation from acetone/petroleum ether
**after reprecipitation from isopropanol/petroleum ether
***after being worked up

EXAMPLE 13

The formulation indicated below is milled on mixing rolls for 5 minutes at 180° C. Samples of sheeting from the resulting rough sheet, 0.3 mm thick, are subjected to heat at 180° C. in a testing oven. The Yellowness Index (YI) of the samples is determined as specified in ASTM D 1925-70 at regular intervals of time. The results are shown in Table 1.

| Formulation: | |
| --- | --- |
| S-PVC (K-value 64) | 100 parts |
| Epoxidized soya bean oil | 3 parts |
| Didecyl phenyl phosphite | 0.55 part |
| Calcium stearate | 0.35 part |
| Zinc stearate | 0.15 part |
| Additive as shown in Table 1 | 0.3 part |

TABLE 1

| Additive | YI after minutes exposure time | | | | |
| --- | --- | --- | --- | --- | --- |
| | 0 | 5 | 10 | 15 | 20 |
| none | 20.4 | 30.9 | 34.3 | 34.9 | 30.3 |
| A | 2.8 | 4.4 | 5.8 | 8.0 | 14.1 |
| B | 4.7 | 6.4 | 8.8 | 11.6 | 14.4 |
| C | 3.7 | 5.0 | 6.9 | 9.8 | 15.5 |
| D | 2.6 | 4.1 | 5.8 | 9.3 | 12.7 |
| E | 2.7 | 4.3 | 5.1 | 8.2 | 10.6 |

A 2,4-bis-(2-hydroxyethylamino)-6-anilino-1,3,5-triazine
B 2,4-bis-(2-hydroxyethylamino)-6-(3-hydroxyanilino)-1,3,5-triazine
C 2,4-bis-(2-hydroxyethylamino)-6-(2-chloroanilino)-1,3,5-triazine
D 2,4-bis-(2-hydroxyethylamino)-6-(3-chloroanilino)-1,3,5-triazine
E 2,4-bis-(2-hydroxyethylamino)-6-(4-chloroanilino)-1,3,5-triazine

EXAMPLE 14

The formulation indicated below is milled on mixing rolls for 5 minutes at 190° C. Samples of sheeting from the resulting rough sheet, 0.3 mm thick, are subjected to heat at 180° C. in a testing oven. The Yellowness Index (YI) of the samples is determined as specified in ASTM D 1925-70 at regular intervals of time. The results are shown in Table 2.

| Formulation: | |
| --- | --- |
| S-PVC (K-value 64) | 100 parts |
| Dioctyl phthalate (plasticizer) | 17 parts |
| Epoxidized soya bean oil | 3 parts |
| Zinc dioleate | 0.5 part |
| Barium bis-[p-t-butylbenzoate] | 0.54 part |
| Didecyl phenyl phosphite | 0.64 part |
| 2,6-di-t-Butyl-4-methylphenol | 0.06 part |
| Oleic acid | 0.02 part |
| Additive as shown in Table 2 | 0.2 part |

TABLE 2

| Additive | YI after minutes exposure time | | | | | |
| --- | --- | --- | --- | --- | --- | --- |
| | 0 | 10 | 20 | 30 | 40 | 50 |
| none | 8.4 | 15.2 | 23.2 | 28.2 | 26.4 | 26.9 |
| F | 2.8 | 4.2 | 5.7 | 5.9 | 9.3 | 12.4 |
| G | 4.2 | 6.5 | 8.0 | 9.9 | 10.9 | 16.4 |
| H | 3.5 | 4.4 | 5.9 | 7.1 | 10.5 | 11.5 |

F 2,4-bis-(2-hydroxyethylamino)-6-(4-methylanilino)-1,3,5-triazine
G 2,4-bis-(2-hydroxyethylamino)-6-(2-methoxyanilino)-1,3,5-triazine
H 2,4-bis-(2-hydroxyethylamino)-6-(3-methoxyanilino)-1,3,5-triazine

What is claimed is:

1. A chlorine-containing polymer which is sensitive to degradation induced by light and/or heat and which contains an effective stabilizing amount of at least one compound of the formula I

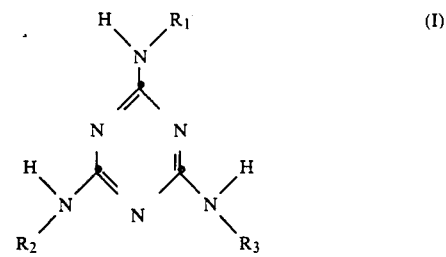

in which $R_1$ is phenyl or a group of the formula II

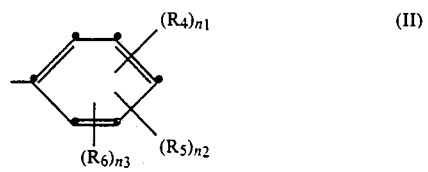

in which $R_4$, $R_5$ and $R_6$ independently of one another are chlorine, bromine, cyano, methoxycarbonyl, ethoxycarbonyl, carbamoyl, hydroxyl, methoxy, ethoxy or $C_1$–$C_{18}$-alkyl and $n_1$, $n_2$ and $n_3$ are 0, 1, 2 or 3, subject to the proviso that the sum of $n_1+n_2+n_3$ is an integer from 1 to 3, and $R_2$ and $R_3$ independently of one another are $C_2$–$C_4$-hydroxyalkyl.

2. A chlorine-containing polymer according to claim 1, in which $R_1$ is phenyl or a group of the formula II in which $R_4$, $R_5$ and $R_6$ independently of one another are chlorine, bromine, hydroxyl, methoxy, ethoxy or $C_1$–$C_{18}$-alkyl.

3. A chlorine-containing polymer according to claim 1, in which $R_1$ is phenyl or a group of the formula II in which $R_4$, $R_5$ and $R_6$ independently of one another are chlorine, hydroxyl, methoxy, ethoxy or $C_1$–$C_{12}$-alkyl.

4. A chlorine-containing polymer according to claim 1, in which $R_1$ is phenyl or a group of the formula II in which $R_4$, $R_5$ and $R_6$ independently of one another are chlorine, hydroxyl, methoxy or methyl.

5. A chlorine-containing polymer according to claim 1, in which $R_1$ is phenyl or a group of the formula II in which the radicals $R_4$, $R_5$ and $R_6$ are identical.

6. A chlorine-containing polymer according to claim 1, in which $R_1$ is phenyl or a group of the formula II in which $n_1$ and $n_2$ are 0 and $n_3$ is 1.

7. A chlorine-containing polymer according to claim 1, in which $R_1$ is phenyl.

8. A chlorine-containing polymer according to claim 1, in which $R_2$ and $R_3$ are 2-hydroxyethyl.

9. A chlorine-containing polymer according to claim 1, containing, in addition, at least one Me(II) carboxylate and/or Me(II) phenate or alkylphenate in which Me(II) is Mg, Ca, Ba, Zn or Cd and carboxylate is the anion of a carboxylic acid having 7 to 20C atoms.

10. A chlorine-containing polymer according to claim 9, wherein the Me(II) carboxylate is a mixture of a barium/zinc, calcium/zinc or magnesium/zinc carboxylate.

11. A chlorine-containing polymer according to claim 1, wherein the chlorine-containing polymer is polyvinyl chloride.

12. A process for stabilizing chlorine-containing polymers against the harmful effects of light and/or heat, which comprises incorporating into the chlorine-containing polymer an effective stabilizing amount of at least one compound of the formula I according to claim 1.

* * * * *